United States Patent
Wilhelmy

Patent Number: 6,073,631
Date of Patent: Jun. 13, 2000

[54] SAFE CROSS CUFFS

[76] Inventor: John Wilhelmy, 109 Canada Via, Diablo, Calif. 94528

[21] Appl. No.: 08/828,359

[22] Filed: Mar. 28, 1997

Related U.S. Application Data

[60] Provisional application No. 60/019,888, Jun. 17, 1996.
[51] Int. Cl.[7] .................................................. A61F 5/37
[52] U.S. Cl. ............................................ 128/878; 128/879
[58] Field of Search ..................................... 128/846, 869, 128/877, 878, 879; 602/21–23; 70/16, 17, 30

[56] References Cited

U.S. PATENT DOCUMENTS

| | | | |
|---|---|---|---|
| D. 366,129 | 1/1996 | Escoe . | |
| 973,330 | 10/1910 | Wood | 128/879 |
| 2,645,922 | 7/1953 | Martin | 128/878 |
| 3,618,345 | 11/1971 | Smith | 70/16 |
| 4,697,441 | 10/1987 | Allen . | |
| 4,854,138 | 8/1989 | Charland . | |
| 4,977,625 | 12/1990 | Charters, III . | |
| 5,205,142 | 4/1993 | Krueger et al. . | |
| 5,233,848 | 8/1993 | Elam . | |
| 5,360,019 | 11/1994 | Witzel | 128/818 |
| 5,461,890 | 10/1995 | LeFavor . | |
| 5,463,884 | 11/1995 | Woo et al. . | |
| 5,479,943 | 1/1996 | Kuhnell, III . | |
| 5,551,086 | 9/1996 | Albanse . | |

*Primary Examiner*—Michael A. Brown

[57] ABSTRACT

The present invention comprises cuffing means supplied with separately attached or integrally molded extensions, wherein each extension has secured or integrally molded thereto at least one part of an engaging means. It is preferable that the engaging means, when operated as attachments to each extension, comprise a quickly latchable or releasable mechanism or manufactured piece.

20 Claims, 4 Drawing Sheets

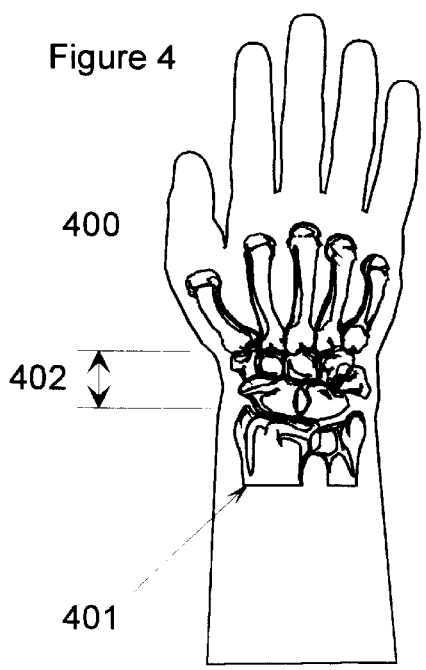
Figure 4
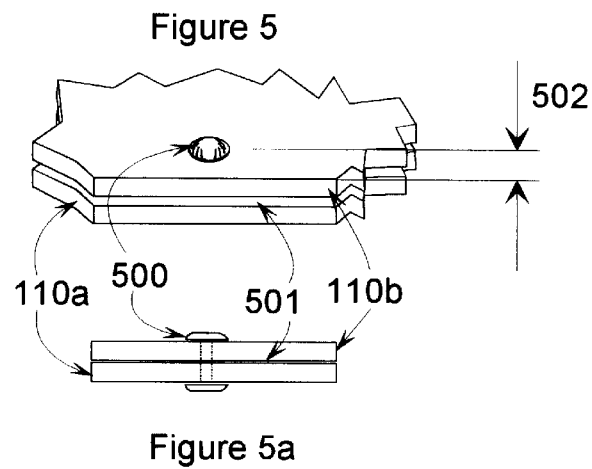
Figure 5
Figure 5a
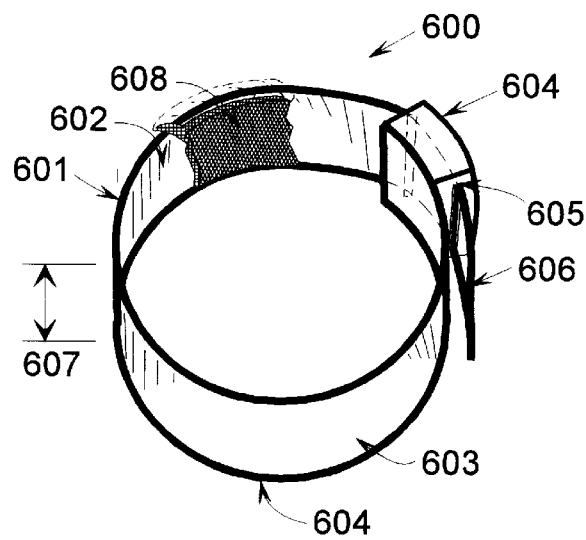
Figure 6

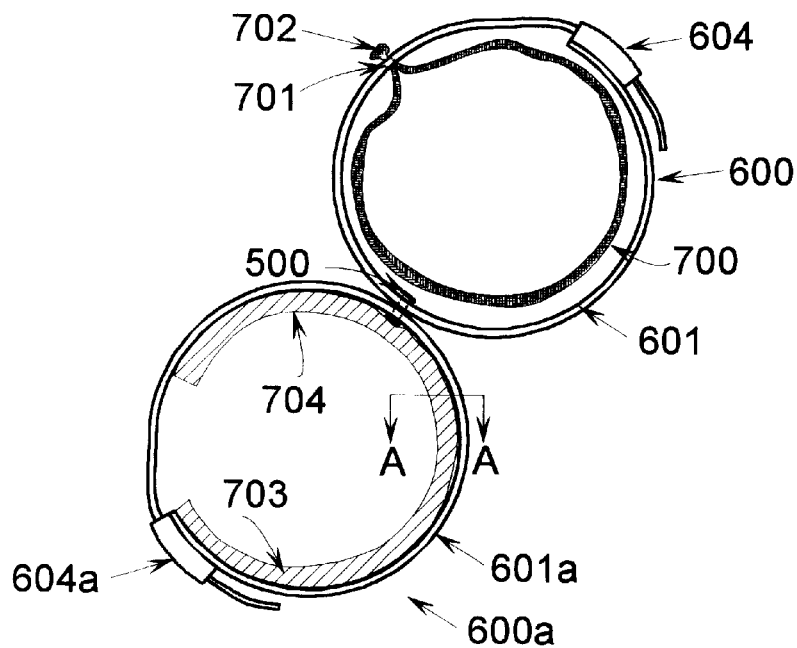
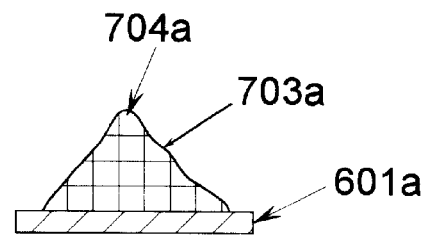
Figure 8a
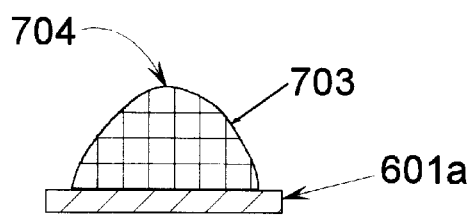
Figure 8

SAFE CROSS CUFFS

This application claims benefit of a prior provisional patent application, Ser. No. 60/019,888, filed Jun. 17, 1996.

BACKGROUND OF THE INVENTION

The present invention relates to wrist or lower arm encircling devices whereby the latching together of the devices restrains the motion or use of the hands and/or arms of a person. The present invention further relates to quickly releasable engaging means for latching or disengaging a first and second cuffing means.

PRIOR ART

The prior art discloses several devices which are used to secure the wrists of a detainee. One of the common failings of these devices lies in their most appropriate use. The hinged handcuffing devices are primarily directed to use for securing the wrists in front of the body instead of behind it. The typical violent detainee generally must have their wrists secured at the section of the midsection body circumference defined from one hip, around the back and then to the other hip. Permitting the violent or potentially violent detainee to have their wrists secured to wrist-encircling devices which are attached only to each other encourages use of the arms and hands as weapons for bludgeoning persons, property and harm to the detainee as well.

U.S. Pat. No. 5,479,943 discloses a handcuff shield for covering a pair of handcuffs to prevent the handcuffs from touching the skin of the user and transmitting viruses and bacteria from the handcuff to the user, each of the pair of handcuffs being covered by the handcuff shield having an arcuate casing and an arcuate blade pivotally connected thereto for encircling a wrist of a person to whom the handcuffs are attached, the arcuate blade being receivable and lockable in the casing, the handcuff shield including a first body section having a bottom and two sidewalls extending upwardly therefrom for covering the arcuate casing, a second body section having a bottom and two sidewalls extending upwardly therefrom for covering the arcuate blade, and a flexible joint connecting the first body section to the second body section.

U.S. Pat. No. 5,463,884 discloses a handcuff for dual use as a quick-release training device and an actual restraint device, which has a bail and an arcuate ratchet member with teeth. The handcuff includes a locking assembly, disposed within a bail, that has a pawl having a first end pivotally coupled to the bail and a second end with teeth pivotal between a secured position in which the teeth of the pawl engage the teeth of the ratchet member and an unsecured position in which the second end of the pawl is separated from the ratchet member. The second end of the pawl further has a vertical shoulder for engagement with the flange of a key inserted within the locking assembly for manipulating the pawl between the secured and unsecured positions upon rotation of the key. A stop member is disposed above the pawl and movable in and out of contact with the pawl upon engagement with the key to prevent the pawl from being placed in the unsecured position when the stop member is in contact with the pawl. A quick-release feature is provided for placing the pawl in the unsecured position when the stop member is not in contact with the pawl.

U.S. Pat. No. 5,461,890 is a handcuff assembly comprising a first wrist encircling means for selectively encircling one wrist, a second wrist encircling means for selectively encircling a second wrist, and a connecting means for rigidly connecting the first wrist encircling means to the second wrist encircling means. The connecting means comprises an elongated body having an opening therein suitable for acting as a receptacle for a hand to allow the connecting means with opening to serve as a device to acquire leverage over the detainee whose wrists are secured in the shackles.

U.S. Pat. No. 5,233,848 discloses a handcuff restraining apparatus including 1) a main handcuff assembly of a rigid, solid construction; 2) pivotal clasp members mounted on respective outer ends of the main handcuff assembly for clasping on a person's wrist area for apprehending and restraining purposes; and 3) a handle cover assembly mounted about the main handcuff assembly and providing an area for ease of holding and firmly grasping. The main handcuff assembly is provided with spaced upper and lower support plate members interconnected in a rigid manner and having aligned chain receiving openings to receive a restraining chain member therethrough.

U.S. Pat. No. 5,205,142 discloses a handcuff device for restraining the wrists of a detainee. The device comprises a pair of handcuff members and a link member of unitary construction. Each of the handcuff members have one or more integrally formed mounting posts. The link member is configured to hingedly interconnect the handcuff members about the posts. The unitary construction of the link member, combined with the integrally formed posts of the handcuff members, provide a handcuff device which is strong and durable and which does not require the use of multiple components, such as a pivot pin, and substantially limits the movement of the detainee's hands.

U.S. Pat. No. 4,977,625 discloses an under-cuff protective device is formed to be placed and retained between a restraining device, such as handcuffs or leg-cuffs, and the detainee. The device includes a flexible base member of a length to substantially encircle the limb, generally at the wrist or ankle. Two wall members are attached to the outside of the base member in longitudinally spaced relationship, separated so as to permit the restraining device to fit between the wall members and snugly about the base member. The wall members form a wall-like structure which retains the restraining device in place on the base member. A preferred means of forming each wall member is by longitudinally folding a portion of the base member over onto its outside surface and attaching it there. The base member is fastened about the detainee's limb using two flexible connecting straps. Hook and loop fastening means are preferred. The connecting straps may be attached to the base member so as to be vertically aligned with the wall member, thus increasing the effective height of the wall member.

U.S. Pat. No. 4,697,441 A pair of wrist shackles or handcuffs in which one handcuff is joined to a second handcuff by a single pivot member that permits one handcuff to pivot or rotate in a planar direction to overlay the other handcuff.

U.S. Pat. No. D366,129 discloses a "Flex-O-Cuff" device comprising two substantially angularly flexible bands drawn into separate loops within which to secure the hands of a detainee. Fixed ends of the flexible bands are fixed to a piece through which are drawn the ends and a portion of the flexible bands to accomplish securing wrists of a detainee.

There is a need in the prior art for

SUMMARY OF THE INVENTION

The present invention comprises cuffing means supplied with separately attached or integrally molded extensions, wherein each extension has secured or integrally molded thereto at least one part of an engaging means. It is preferable that the engaging means, when operated as attachments to each extension, comprise a quickly latchable or releasable mechanism or manufactured piece. It is further preferable that (1) a first engaging means for a first cuffing means comprise, generally, a laterally threaded bolt, wherein one end of the bolt is secured to an extension of the first cuffing means and (2) a second engaging means for a second cuffing means comprise, generally, a reception unit for the laterally threaded bolt, wherein the reception unit is secured to an extension of the second cuffing means. The arrangement of the extensions and the engaging means are a critical improvement over the prior art and are described as follows.

When the cuffing means are in place on the wrists or lower arms of a person who will be restrained, they form generally cylindrical (or slightly conical), stiff supports for the extensions. It is preferable to arrange the extensions such that they extend from the rim area of the generally cylindrical support of the cuffing means situated closest to the wrist of the person. When the first and second engaging means are engaged, the distance between the rim areas of the generally cylindrical support of the cuffing means situated closest to the wrist of the person is sufficiently small to force the wrists or lower arms of the person to remain in a crossed arrangement restraining the wrists and lower arms movement of the person in a manner far superior than that of prior art handcuffs. To achieve this object, the extensions are preferably short or are merely attachment points of the engaging means and the height of the engaged first and second engaging means assembly situated between the extensions is preferably minimized.

It is known in the art of attaching prosthetic devices that a threaded bolt and reception unit provide a very effective connection device which resists lateral, vertical and torsional pulling and pushing forces associated with human motion. It is preferable in the present invention to use such devices for engaging means, which will withstand the sometimes violent instantaneous or sustained pulling and pushing forces to be expected from the arm movement of the restrained person. A release mechanism is generally used with wrist restraint devices, and the disclosures of the prior art are generally incorporated herein for suggesting such release mechanisms for the engaging means. It is, however, preferable that the bolt situated in the reception unit be releasable by action of a retraction lever inaccessible to the restrainee. It is further preferably the lever be locked in position, wherein the locking mechanism requires a separate unlocking piece or key to permit operation of the lever.

The arm crossing function of the present invention in operation leaves the hands free to protect the restrainee from falls or to pick up objects, although generally incapable of manipulating the unlocking piece to obtain unassisted release of the engaging means. Advantageously reducing to a minimum the engaged distance between the wrist rim areas of the cuffing means reduces the field of movement within which the restrainee may swing his arms as compared with prior art handcuffs. This is an object of improved protection for the one charged with overseeing the restrainee.

It is preferable that the cuffing means further comprise a minimal layer of padding between the arm and wrist of the restrainee and the portion of the cuffing means providing effective support for the extensions and engaging means. The support portion of the cuffing means can comprise a frame, longitudinal or lateral bands or a solid or hinged solid generally cylindrical mechanism or manufacture. It is preferable that the support portion of the cuffing means comprise a tough, resilient, and relatively plastic slightly conical solid cylinder, wherein the extensions are located near the rim area with the smaller diameter. It is further preferred that the cylinder be split longitudinally to accommodate a hinge in one split and closing means to secure the cuffing means about the wrist and lower arm of the restrainee. The closing means are preferably a zip-tie flexiwrap band or bands which are releasable or only for one-way draw-through locking in successively smaller diameter positions. Alternatively, it is preferred that the closing means comprise a releasable strap held in attached to one side of the non-hinged split and on the other side is located a latch similar to that found in ski-boots of the present state of the art.

BRIEF DESCRIPTION OF THE DRAWINGS

FIG. 4 is the outline of a human hand and forearm and showing the bones of the wrist, forearm and hand associated with wrist encircling means.

FIGS. 5 and 5a are edge close-up views of two wrist encircling means at a circumferential edge proximal to the wrist on application wherein the two wrist encircling means are close coupled.

FIG. 6 is a wrist encircling means wherein the width of the wrist encircling means is passed through a closure latching means. An incomplete section of abrasion-reducing layer of padding is shown on the interior surface of the wrist encircling means.

FIG. 7 shows two wrist encircling means substantially as in FIG. 6 close coupled and providing additional wrist securing by different wrist securing means in each wrist encircling means.

FIGS. 8 and 8a are cross-sectional views of one of the wrist encircling means and wrist securing means shown in FIG. 7.

DETAILED DESCRIPTION OF THE INVENTION

Figure 1:
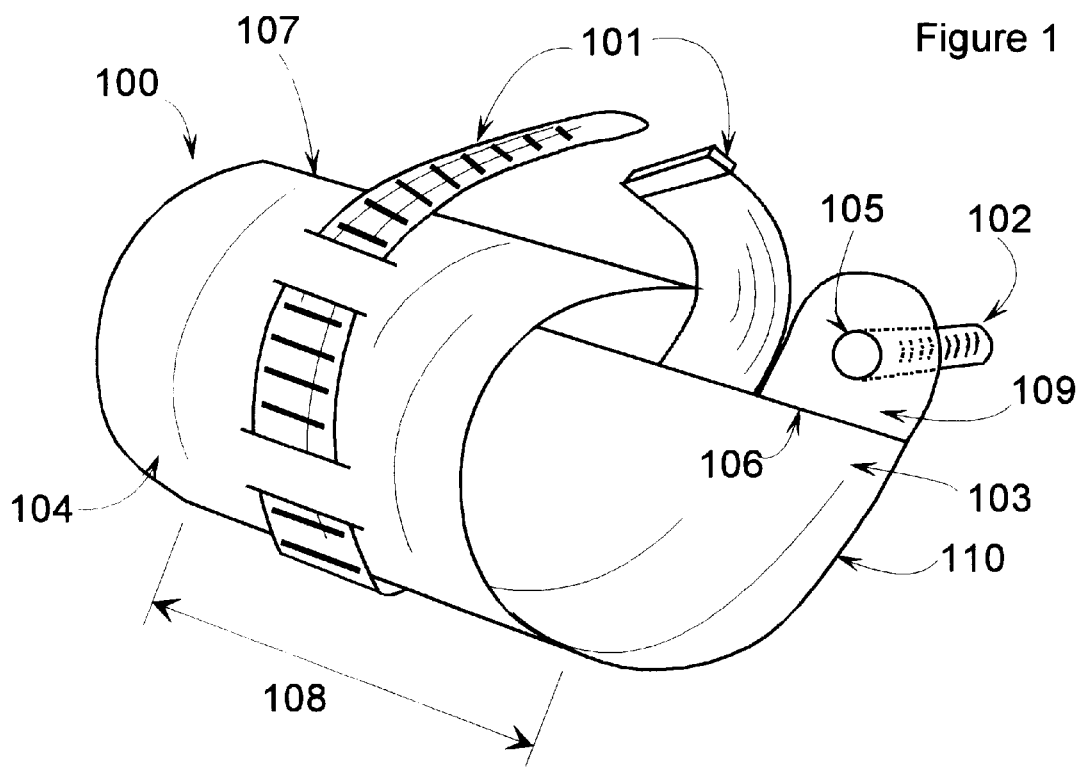
FIG. 1 shows the first cuffing or wrist encircling means with an extension and first engaging or rotating means.

The present invention is now discussed with reference to FIG. 1. First cross cuff means 100 is shown wherein generally cylindrical wrist encircling means 104 is open along a longitudinal split along longitudinal edges 106 and 107 to accommodate placement of a restrainee's lower arm and wrist in the interior 103 of the generally cylindrical wrist encircling means 104. The interior 103 preferably has attached to it, removably or permanently, padding such as rubber foam, foam-filled cloth envelopes or similar compressible cellular material to accommodate firm restraint of a detainee while reducing possibility of harm from violent movement. Longitudinal length 108 is the effective restraining length of wrist encircling means 104 which is to be applied to the detainee such that wrist circumferential edge 110 defines a circumference close to the juncture of the hand and wrist bones.

Extension 109 is shown extending from the wrist circumferential edge 110 area of wrist encircling means 104, although preferably extending downwardly from the corner of the wrist circumferential edge 110 and edge 107. Threaded bolt 102 is attached to extension 109 at attachment 105. Closing means 101 is generally a zip-tie flexiwrap band, wherein the tapered end of closing means 101 is inserted into the other, sequentially latching at each subsequent raised notch or slot until its end and drawn therethrough and firm support of extension 105 is achieved in relation to and after placement of the restrainee's arm against the interior 103. Latching means may be adequately adapted from devices in the prior art, as shown in U.S. Pat. No. 5,463,884, which is incorporated herein. The disclosure of that patent is of a ratchet and spring actuated pawl used for a wrist encircling and locking device, which may be made with molded ratchet notches on closing means 101 or such similar embodiments of the present invention wherein latching means or latching action is required. It will be obvious from the nature of the device herein that a further locking mechanism should be associated with the ratchet and pawl latching means so that a detainee cannot easily unlock the wrist encircling devices of the present invention. Examples of locking mechanisms are those that require key release or may simply be inaccessible to a detainee restrained with the devices of the present invention, although preferably easily releasable by detaining personnel.

Figure 2:
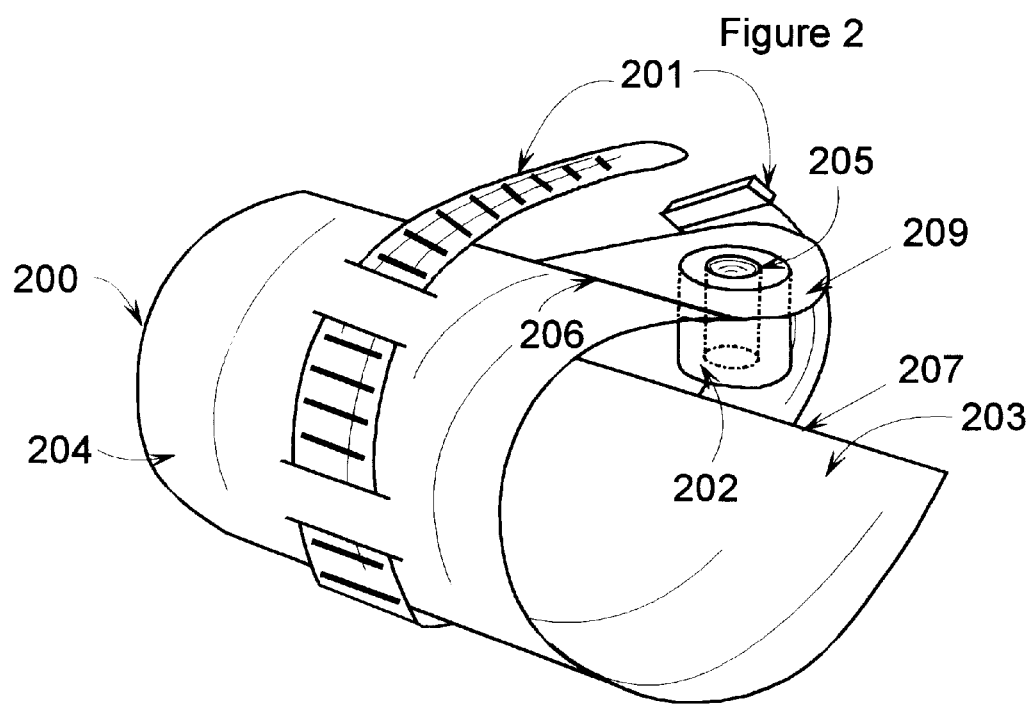
FIG. 2 shows the second cuffing or wrist encircling means with an extension and second engaging or rotating means.

The present invention is now discussed with reference to FIG. 2. Second cross cuff means 200 is shown wherein generally cylindrical wrist encircling means 204 is open along a longitudinal split along longitudinal edges 206 and 207 to accommodate placement of a restrainee's lower arm and wrist in the interior 203 of the generally cylindrical wrist encircling means 204. The interior 203 preferably has attached to it, removably or permanently, padding such as rubber foam, foam-filled cloth envelopes or similar compressible cellular material to accommodate firm restraint of a detainee while reducing possibility of harm from violent movement.

Extension 209 is shown extending from the rim area of wrist encircling means 204, although preferably extending downwardly from the corner of the cylinder rim and the longitudinal split. Reception unit 202 is attached to extension 209 at attachment 205. Closing means 201 is generally a zip-tie flexiwrap band, wherein the tapered end of closing means 201 is inserted into the other, latching end and drawn therethrough until firm support of extension 209 is achieved in relation to and after placement of the restrainee's arm against the interior of wrist encircling means 204.

Figure 3:
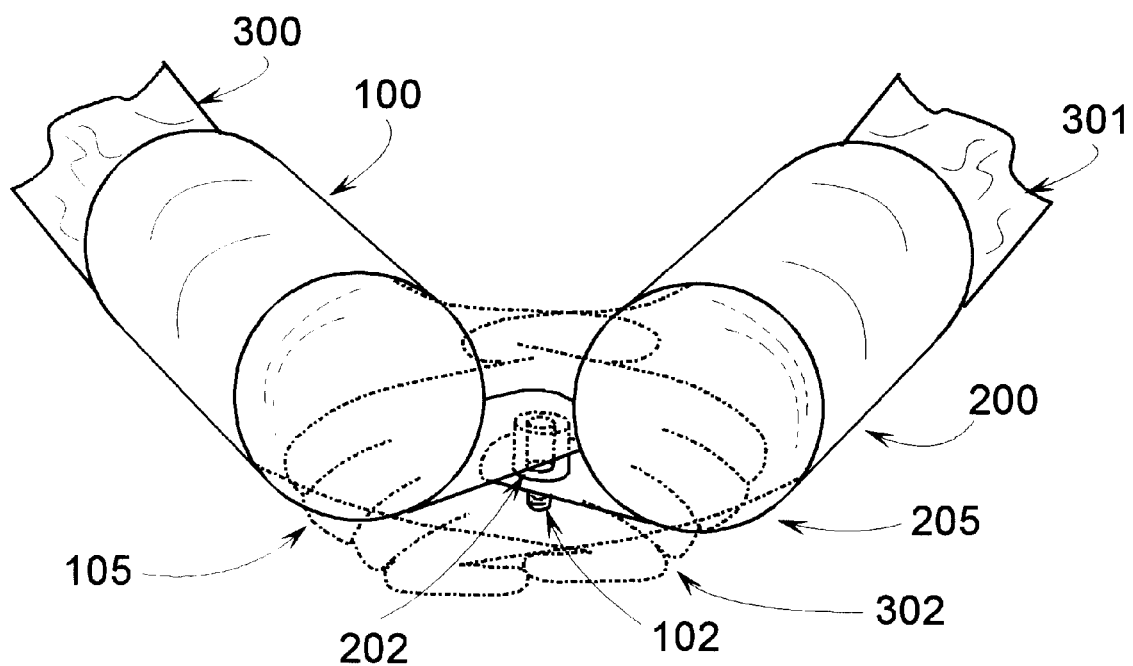
FIG. 3 shows the engaged assembly of the engaging or rotating means with the cuffing or wrist encircling means and the lower arms and hands of a restrainee.

The present invention is now discussed with reference to FIG. 3. First cross cuff means 100 is shown secured to the lower arm 300 of a restrainee. Second cuffing means 200 is shown secured to the other lower arm 301 of the restrainee. The engagement (rotation) means of the first and second cross cuff means are shown engaged in an assembly forcing the crossing of the restrainee's arms generally in a crossed orientation in the area of the wrists. This engagement means assembly has been formed by insertion of threaded bolt 102 into receptor unit 202, each of which is respectively the engagement or rotating means of the first and second cross cuff means. It will be observed in FIGS. 1, 2 and 3 that the orientation of threaded bolt 102 on extension 109 with respect to the receptor unit 202 on extension 209 is to an insertion axis of the threaded bolt 102 into receptor unit 202 which is generally parallel to the axis of the restrainee's body, permitting easy engagement of the engaging means for the violent restrainee. The close relationship of the wrists and lower arms of the restrainee are seen in FIG. 3 to be of such a short distance to prevent manipulation of the engagement means assembly, thereby eliminating the potential of unassisted release from the cuffing and engagement means.

It will be appreciated that the above described rotating means may be designed in many ways to achieve the objects of the present invention, especially to obtain a substantially inflexible rotational connection between the wrist encircling means in the area of the wrist circumferential edge, preferably about within 2 inches of the wrist circumferential edge. This rather close location of the substantially inflexible rotational connection to the detainee's wrists permits a surprisingly effective distribution of force from violent movements of the detainee over a broad surface area on the arm instead of concentrating such movement to a handcuff or other such prior art device.

FIG. 4 shows in hand 400 forearm/wrist/hand bones 401 such that an appreciation of the rather narrower circumference of wrist zone 402 may be had with respect to the effectively greater diameter bone structures of the adjacent forearm and hand. It can be seen that restraint of the hand and/or arm can be improved by securing the wrist with an encircling device which is smaller in circumference than the immediately adjacent forearm and hand bone structure. This observation implies that such an encircling device has width less than or equal to that of wrist zone 402.

FIG. 6 shows another embodiment of the present invention. Wrist encircling means 600 comprises a relatively stiff band of material which can be brought into cylindrical enclosure about the wrist of a detainee. The width 607 is preferably equal to or greater than about 0.5 inches. In widths less than about 1.5 inches for width 607, the embodiment of FIG. 5 is preferred wherein free end 606 is drawn through latching slot 605 of latching means 604 at the end of wrist encircling means 600 distal to free end 606. Wrist circumferential edge 601 is, on application to a detainee, located substantially as described for edge 110 in FIG. 1. Exterior surface 603 is preferably smooth but may comprise a padded surface above the relatively stiff band to protect detaining personnel from blows from the detainee. Interior surface 602 may be without protection between the skin of the detainee, but preferably comprises an additional layer of chafing-resistant material or padding with material exhibiting resiliency or elastic rebounding capacity as shown in part in insert 608. Insert 608 shows in part a protective piece that preferably extends along interior surface 602 from the latching means 604 end only so far as not to interfere with the securing of wrist encircling means 600 by drawing free end 606 through latching means 604.

FIGS. 5 and 5a show a section of wrist encircling means such as shown in FIGS. 1, 2, 3, and 6 embodying close coupling rotating means. The shaft and capping means 500, another embodiment of rotating means for the present invention, secures exemplary sections of two wrist encircling means with wrist circumferential edges 110a and 110b. Substantially no or very little space 501 is left between the facing surfaces of the two wrist encircling means adjacent to the shaft and capping means 500, the shaft of which pierces the relatively stiff bands of the two wrist encircling means. The facing exterior surfaces of the two wrist encircling means are joined by shaft and capping means 500 such that the two wrist encircling means may rotate substantially only about the axis of the shaft of the shaft and capping means 500. This makes possible a very close association of the wrists of a detainee, making most comfortable a position in the detainee of one wrist or forearm located above another wrist or forearm. It has been found that an optimum rotating means securing distance 502 from the wrist circumferential edges is about 0.5 inches.

In FIG. 7, wrist encircling means 600 and 600a are closely coupled at shaft and capping means 500 as shown in FIGS. 5 and 5a. In a further set of embodiments of the present invention, wrist encircling means 600 is provided with wrist securing means 700, comprising a strong, loop of flexible material adapted to be drawn about the detainee's wrist zone 402, as shown in FIG. 4, wherein the ends of the loop of material are arranged such that one or more of the ends may be drawn through a hole 701 in the relatively stiff band and to the exterior of the band to form loop stay means 702. Such stay means are shown and described in U.S. Pat. Nos. 4,854,138 and D366,129, which are incorporated herein. This loop and stay embodiment provides wrist securing means attached to the wrist encircling means to better restrain unpermitted removal of detainee's hand from restraint.

Another embodiment for prevention of unpermitted removal of detainee's hand from restraint is shown in FIG. 7 in relation to wrist encircling means 600a. Annular compression piece 703 comprises a firm, slightly yielding material (such as neoprene or butyl or natural rubber) with a ridge 704, which will preferably compressingly lie within wrist zone 402, as shown in FIG. 4, upon application of the wrist encircling means 600a to a detainee. Cross-section AA is shown in FIGS. 8 and 8a as examples of preferred forms of ridge 704 and 704a for annular compression pieces 703 and 703a.

Other design options will sometimes present the designer with considerable and wide ranges from which to choose appropriate modifications for the above examples. However, the objects of the present invention will still be obtained by the skilled person applying such design options in an appropriate manner.

I claim:

1. A cross cuff restraining device comprising:
   a) two separate wrist encircling means each comprising a releasable and relatively stiff band greater than about 0.5 inches wide and adapted to secure within each wrist encircling means at least a wrist of a detainee; and
   b) rotating means for close coupling the wrist encircling means to each other such that there is less than about 0.5 inches between closest facing surfaces of the wrist encircling means.

2. The cross cuff restraining device of claim 1 wherein the rotating means further comprise a short shaft piercing the relatively stiff bands and capping the shaft with capping means whereby the rotating means are adapted to compel slidable contact between the closest facing surfaces of the wrist encircling means.

3. The cross cuff restraining device of claim 1 wherein the rotating means further comprise a shaft piercing the relatively stiff bands, providing rotatable attachment of shaft ends to the closest facing surfaces of the wrist encircling means such that essentially no contact is made between the closest facing surfaces of the wrist encircling means.

4. The cross cuff restraining device of claim 3 wherein the shaft comprises means for disengagement of the shaft into first and second shaft pieces such that the first shaft piece remains in rotatable attachment to one wrist encircling means and the second shaft piece remains in rotatable attachment with the other wrist encircling means.

5. The cross cuff restraining device of claim 4 wherein the first shaft piece is a threaded shaft and the second shaft piece comprises means for releasably receiving the threaded shaft.

6. The cross cuff restraining device of claim 2 wherein secured to each wrist encircling means is a wrist securing means less than about 0.5 inches wide and adapted to further restrain a detainee such that the wrist securing means encircle substantially only the wrists of a detainee with a smaller diameter than that of the wrist encircling means.

7. The cross cuff restraining device of claim 6 wherein the attachment of the wrist securing means to the wrist encircling means is made integral with the shaft and capping means for that same wrist encircling means.

8. The cross cuff restraining device of claim 6 wherein the attachment of the wrist securing means to the wrist encircling means is made within about 2.0 inches from a circumferential edge of the wrist encircling means.

9. The cross cuff restraining device of claim 6 wherein each wrist securing means comprises an attachable loop of flexible braid, flexible solid polymer or fiber-reinforced elastomer.

10. A cross cuff restraining device comprising:
    a) two separate wrist encircling means each comprising a releasable and relatively stiff band greater than about 0.5 inches wide and adapted to secure within each wrist encircling means a wrist and at least a portion of a forearm of a detainee; and
    b) attachment means attaching together the wrist encircling means at a point on the wrist encircling means closer to one circumferential edge than to the other.

11. The cross cuff restraining device of claim 10 wherein attachment means attach to each wrist encircling means within about 3 inches of a first circumferential edge of each wrist encircling means, which first circumferential edge is adapted to be proximate to the hand of a detainee.

12. The cross cuff restraining device of claim 10 wherein each band of the wrist encircling means is more than about 2 inches wide.

13. The cross cuff restraining device of claim 10 wherein each band of the wrist encircling means is more than about 6 inches wide.

14. The cross cuff restraining device of claim 13 wherein a band of flexible material is slidably attached circumferentially about a center section of each wrist encircling means and is adapted to releasably cinch each wrist encircling means about at least a wrist and part of a forearm of a detainee.

15. The cross cuff restraining device of claim 10 wherein the attachment means comprise means for disengagement of the shaft into first and second shaft pieces such that the first shaft piece remains in rotatable attachment to one wrist encircling means and the second shaft piece remains in rotatable attachment with the other wrist encircling means.

16. The cross cuff restraining device of claim 15 wherein the first shaft piece is a threaded shaft and the second shaft piece comprises means for releasably receiving the threaded shaft.

17. The cross cuff restraining device of claim 10 wherein secured to each wrist encircling means is a wrist securing means less than about 0.5 inches wide and adapted to further restrain a detainee such that the wrist securing means encircle substantially only the wrists of a detainee with a smaller diameter than that of the wrist encircling means.

18. The cross cuff restraining device of claim 17 wherein each wrist securing means comprises an attachable loop of flexible braid, flexible solid polymer or fiber-reinforced elastomer.

19. The cross cuff restraining device of claim 10 wherein the attachment means attach to each wrist securing means along a longitudinal edge of a longitudinal opening of each wrist securing means.

20. The cross cuff restraining device of claim 10 wherein each wrist securing means has an interior surface adapted to closely associate with at least the wrist and forearm of a detainee, wherein is interposed between the skin of the detainee and the interior surface an anti-chafing/padding barrier which is attached to the interior surface.

* * * * *